US006972026B1

(12) United States Patent
Caldwell et al.

(10) Patent No.: US 6,972,026 B1
(45) Date of Patent: Dec. 6, 2005

(54) SURGICAL ACCESS DEVICE

(75) Inventors: Martin Caldwell, Dublin (IE); Mike Muntner, Dublin (IE)

(73) Assignee: Gaya Limited, Dublin (IE)

( * ) Notice: Subject to any disclaimer, the term of this patent is extended or adjusted under 35 U.S.C. 154(b) by 0 days.

(21) Appl. No.: 09/936,723

(22) PCT Filed: Mar. 20, 2000

(86) PCT No.: PCT/IE00/00032

§ 371 (c)(1),
(2), (4) Date: Mar. 1, 2002

(87) PCT Pub. No.: WO00/54675

PCT Pub. Date: Sep. 21, 2000

(30) Foreign Application Priority Data

Mar. 18, 1999 (IE) ..................... S990219

(51) Int. Cl.⁷ .............................. A61B 17/34
(52) U.S. Cl. ..................... 606/213; 606/192
(58) Field of Search ................ 606/192, 193, 606/213, 191; 600/207; 604/167.02, 256, 604/167.03, 167.04, 167.01

(56) References Cited

U.S. PATENT DOCUMENTS

| 1,157,202 A | 10/1915 | Bates et al. |
| 3,347,227 A | 10/1967 | Harrower |
| 4,573,576 A | 3/1986 | Krol |
| 4,984,564 A * | 1/1991 | Yuen ........................ 600/207 |
| 5,082,005 A | 1/1992 | Kaldany |
| 5,159,921 A | 11/1992 | Hoover |
| 5,213,114 A | 5/1993 | Bailey, Jr. |
| 5,279,575 A | 1/1994 | Sugarbaker |
| 5,366,478 A | 11/1994 | Candadai et al. |
| 5,514,133 A | 5/1996 | Golub et al. |
| 5,522,791 A * | 6/1996 | Leyva ........................ 600/207 |
| 5,524,644 A | 6/1996 | Crook |
| 5,545,179 A * | 8/1996 | Williamson, IV ........... 606/213 |
| 5,634,911 A | 6/1997 | Hermann et al. |
| 5,634,937 A * | 6/1997 | Mollenauer et al. ........ 606/213 |
| 5,636,645 A | 6/1997 | Ou |
| 5,640,977 A | 6/1997 | Leahy et al. |
| 5,649,550 A | 7/1997 | Crook |
| 5,658,272 A | 8/1997 | Hasson |
| 5,658,306 A | 8/1997 | Kieturakis et al. |
| 5,741,298 A | 4/1998 | Macleaod |
| 5,810,721 A | 9/1998 | Mueller et al. |
| 5,817,062 A | 10/1998 | Flom et al. |
| 5,830,191 A | 11/1998 | Hildwein et al. |
| 5,871,474 A * | 2/1999 | Hermann et al. ........... 604/256 |

(Continued)

FOREIGN PATENT DOCUMENTS

EP          0 487 175 A1     5/1992

(Continued)

Primary Examiner—Anhtuan T. Nguyen
Assistant Examiner—Jessica R. Baxter
(74) Attorney, Agent, or Firm—Nixon Peabody LLP; Tim L. Brackett, Jr.

(57) ABSTRACT

Surgical device (1) is for use in minimally invasive surgery using an inflated body cavity (2) accessible to a surgeon through an access port defined by a sleeve (4) passing through an incision in a patient's abdominal wall (3). The device is held in position by a distal ring (5) and a proximal ring (6). An incision engaging bladder (10) provides a first seal for engaging and retracting the incision when inflated. A second seal is provided by a self engaging bladder (12) for sealing the sleeve (4).

7 Claims, 1 Drawing Sheet

U.S. PATENT DOCUMENTS

Figure 1:
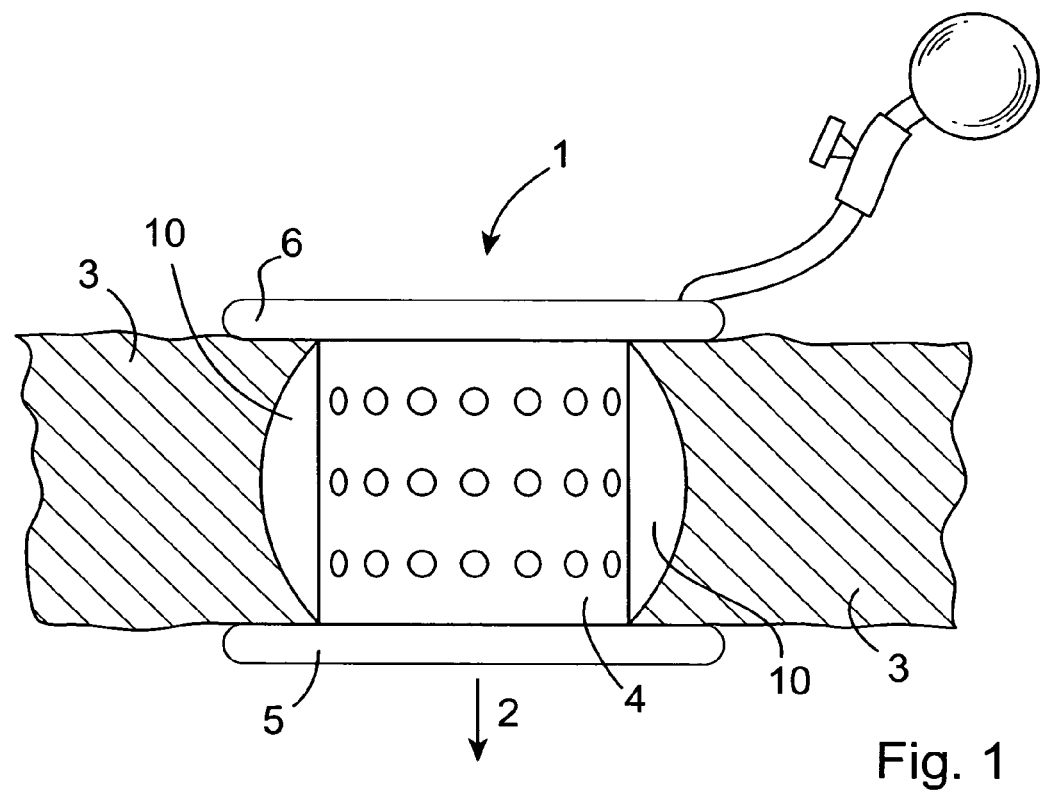

| | | | |
|---|---|---|---|
| 5,882,344 A | 3/1999 | Stouder, Jr. | |
| 5,906,577 A | 5/1999 | Beane et al. | |
| 5,989,232 A | 11/1999 | Yoon | |
| 6,033,426 A * | 3/2000 | Kaji | 606/213 |
| 6,033,428 A | 3/2000 | Sardella | |
| 6,077,288 A | 6/2000 | Shimomura et al. | |
| 6,142,935 A | 11/2000 | Flom et al. | |
| 6,149,642 A | 11/2000 | Gerhart et al. | |
| 6,254,533 B1 | 7/2001 | Fadem et al. | |
| 6,254,534 B1 | 7/2001 | Butler et al. | |
| 6,276,661 B1 | 8/2001 | Laird | |
| 6,382,211 B1 | 5/2002 | Crook | |
| 6,440,063 B1 | 8/2002 | Beane et al. | |
| 6,450,983 B1 | 9/2002 | Rambo | |
| 2001/0037053 A1 | 11/2001 | Bonadio et al. | |

FOREIGN PATENT DOCUMENTS

| | | |
|---|---|---|
| EP | 0 542 428 A1 | 5/1993 |
| GB | 2 103 936 A | 3/1983 |
| GB | 2 275 420 A | 8/1994 |
| WO | WO 95 07056 A | 3/1995 |
| WO | WO-95-11050 A1 | 4/1995 |
| WO | WO-96-10432 A1 | 4/1996 |
| WO | WO 96 36283 A | 11/1996 |
| WO | WO97 31578 A1 | 9/1997 |
| WO | WO-00/32120 A1 | 6/2000 |
| WO | WO-00/35356 A1 | 6/2000 |
| WO | WO-01/26559 A1 | 4/2001 |
| WO | WO-02/34108 A2 | 5/2002 |

* cited by examiner

SURGICAL ACCESS DEVICE

The present invention relates to a surgical device for use in minimally invasive surgery of the type using patient pneumoperitoneum and an access port.

Minimally invasive surgery of this type is carried out having introduced gas into a patient's body cavity through an incision and sealed the incision with an access port. The access port enables laproscopic and hand or instrument assisted surgery to be performed.

A sleeve forming such a port is shown in WO-A-95/07056 entitled "Apparatus for use in surgery". The access port sleeve shown is used to create a controlled pressurized environment within the sleeve while allowing a surgeon's arm to pass through the sleeve. During surgery, gas is pumped into the patient's body cavity where the surgery is to be performed and the sleeve prevents gas escaping while allowing the surgeon to operate using minimally invasive surgery techniques. The application shows a sleeve having a flange at a distal end provided with adhesive for adhering the device to a patient's body or alternatively a mounting ring to surround the incision in a patient's body. While providing a suitable apparatus for performing such surgery the device described suffers from the principle disadvantage that in use, the sleeve protrudes upwardly from the patient and may interfere with the activities of the surgery team. Additionally, the sleeve must be sealed against the surgeon's upper forearm by clamping the device to the arm sufficiently tightly to avoid gas leak around the area of the seal. This presents the surgeon with a problem both in sealing the sleeve and in subsequent mobility.

A further problem associated with the use of sleeves of the kind described is that a phenomenon known as "tenting" may occur. "Tenting" means that when the sleeve is adhered to the patient's skin or to a surgical drape and gas is induced into the patients abdominal cavity, there is a tendency for the sleeve to fill with gas and to pull away from the patient.

International Patent Specification No. WO 96/36283 discloses surgical access devices for sealing an incision and providing a sealed access port for surgical instruments. In one embodiment disclosed in the specification of WO 96/36283, a flexible skin seal is fitted with one or more dumb-bell shaped balloons. These balloons can be inflated after the skin seal is inserted into an incision in the abdomen.

There is therefore a need for a surgical device, which will overcome the aforementioned problems.

Accordingly, there is provided a surgical device for use in minimally invasive surgery of the type using an inflated body cavity accessible to a surgeon through an access port, defined by the device, surrounding an incision in a patient's body, the device having:— distal body cavity engagement means for insertion into the incision to locate the device in position; proximal fixing means for attaching the device to a patients skin; a sleeve connected between the body cavity engagement means and the fixing means defining an access port; and charaterized in that the device includes sealing means, operating on the sleeve to prevent substantial leakage of gas from the body cavity on inflation when in an inoperative position and formed to mould to a substantial portion of a surgeon's hand or surgical instrument on insertion in an operating position, the sealing means being provided by an inflatable first seal for engaging and retracting the incision and a second inflatable seal for sealing the lumen of the tube or sleeve bore.

Ideally, the sleeve is provided by a perforated wall defining a substantially cylindrical tube.

Preferably, the body cavity engagement means is provided by a distal ring formed for insertion into the incision.

Preferably, the fixing means is provided by a proximal ring for engaging with a patient's skin.

In one arrangement, the proximal ring has an associated connector ring for receiving additional seals or medical instruments.

Ideally, the first seal is provided by an inflatable bladder extending outwardly from the sleeve on inflation to form a seal with the incision.

Preferably, the second seal is provided by an inflatable bladder extending inwardly from the tube or sleeve on inflation to prevent excessive loss of gas through the access port.

In a particularly preferred arrangement, the second seal is operatively connected and mounted within the first seal.

The invention will now be described more particularly with reference to the accompanying drawings, which show, by way of example only, an embodiment of a surgical device in accordance with the invention, in which:—

Figure 2:
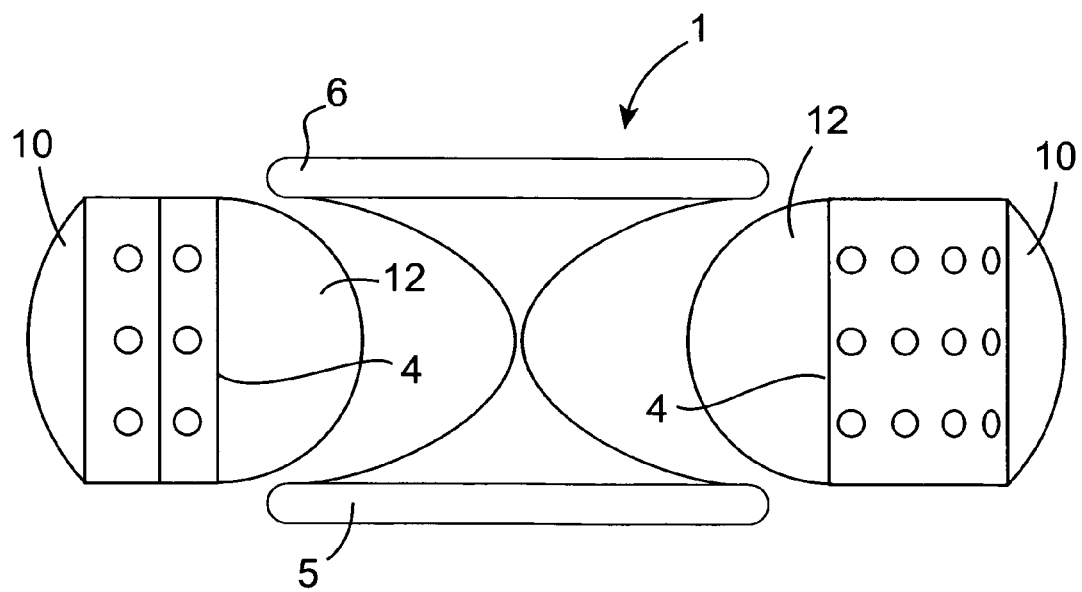

FIG. 1 is a front view of a surgical device in accordance with the invention; and FIG. 2 is an exploded view of the surgical device of FIG. 1.

Referring to the drawings, there is illustrated a surgical device according to the invention, indicated generally by the reference numeral 1. The surgical device 1 is formed for use in minimally invasive surgery of the type using an inflated body cavity indicated generally by the reference numeral 2. The cavity 2 is accessible to a surgeon through an access port, defined by a sleeve 4, passing through an incision in a patient's abdominal wall 3. The sleeve 4 is provided in this case by a perforated wall defining a cylindrical tube.

In more detail, the device 1 has a body cavity engagement means provided by a distal ring 5 for insertion into the incision to locate the device 1 in position. The device 1 is held in position on the patient's skin out side the body by a fixing means provided in this case by a proximal ring 6. The distal ring 5 and proximal ring 6 ensure that the device 1 is securely fixed in position, both rings 5,6 surround the incision and the sleeve 4 passes through the incision connecting the rings.

The proximal ring 6 may have a connector ring (not shown) for receiving additional seals to prevent loss of pressure from the cavity 2. The connector ring may also be used for holding or guiding medical instruments into position over, through or in the incision.

Sealing means is provided to prevent undue loss of gas from the inflated body cavity 2 by a two part inflatable seal. An incision-engaging bladder 10 provides a first seal for engaging and retracting the incision when inflated. A second seal is provided by a self-engaging bladder 12 mounted within the sleeve 4 for sealing the sleeve 4 when similarly inflated. The sleeve 4 separates the incision-engaging bladder 10 and the self-engaging bladder 12. The self-engaging bladder 12 surrounds the internal surface of the sleeve 4 and the external surface of the sleeve 4 is in turn surrounded by the incision-engaging bladder 10 thereby providing a compact unit, which is easy to operate.

In use, an incision is made in the abdominal wall 3 and the distal ring 5 passed through the incision into the cavity 2. The distal ring 5 is moved when in the cavity 2 so that the ring 5 surrounds the incision. The proximal ring 6 is then attached to the patients skin to fix the device 1 in position with the sleeve 4 being connected between the proximal ring 6 and the distal ring 5 and passing between the portions of the abdominal wall 3 exposed by the incision. The incision-engaging bladder 10 and the self-engaging bladder 12 both surrounding the sleeve 4 are also in position passing through the abdominal wall. A hand operated bellows 11 can then pumped to inflate both the incision-engaging bladder 10 and the self-engaging bladder 12. The incision-engaging bladder 10 expands outwardly from the external wall of the sleeve 4 to press against the abdominal wall exposed by the incision to prevent loss of gas from the cavity 2. The self-engaging bladder 12 expands inwardly from the internal wall of the sleeve 4 to close the sleeve 4 against itself thereby preventing loss of gas through the sleeve 4.

When a surgeon wishes to gain access to the cavity 2 a hand or instrument is passed down through the sleeve 4. The inward pressure of the self-engaging bladder 12 ensures that the sleeve is only opened sufficiently to allow the inserted object to pass but prevents loss of pressure from the body cavity. As the object is removed, the same pressure re-seals the sleeve 4 as described above. As a hand or instrument is passed down through the sleeve 4, air or gas is expelled from the bladder 12 through perforations in the sleeve 4. The expelled air or gas is forced into the bladder 10 which expands and further retracts the incision, enhancing the ease of access through the sleeve 4 and incision.

It will be noted that while a bellows or inflating device is described, with air or gas communicating between the incision-engaging bladder and the sleeve-engaging bladder it is anticipated that separate inflation devices for independent control may be used.

It will of course be understood that the invention is not limited to the specific details described herein, which are given by way of example only, and that various modifications and alterations are possible within the scope of the invention.

What is claimed is:

1. A surgical device (1) for use in minimally invasive surgery of the type using an inflated body cavity (2) accessible to a surgeon through an access port, defined by the device (1), surrounding an incision in a patient's body, the device having:

distal body cavity engagement means (5) for insertion into the incision to locate the device in position;

proximal fixing means (6) for attaching the device to a patient's skin;

a sleeve (4) connected between the body cavity engagement means (5) and the fixing means defining an access port; and characterized in that the device includes sealing means (10, 12), operating on the sleeve (4) to prevent substantial leakage of gas from the body cavity (2) on inflation when in an inoperative position and formed to mould to a substantial portion of a surgeon's hand or surgical instrument on insertion in an operating position, the sealing means being provided by an inflatable first seal (10) for engaging and retracting the incision and a second inflatable seal (12) for sealing the lumen of the tube or sleeve bore, in which the sleeve (4) is provided by a perforated wall defining a substantially cylindrical tube.

2. A surgical device (1) as claimed in claim 1, in which the body cavity engagement (5) means is provided by a distal ring (5) formed for insertion into the incision.

3. A surgical device as claimed in claim 1, in which the fixing means is provided by a proximal ring for engaging with a patient's skin.

4. A surgical device (1) as claimed in claim 3, in which the proximal ring (6) has an associated connector ring for receiving additional seals or medical instruments.

5. A surgical device as claimed in claim 1, in which the first seal (10) is provided by an inflatable bladder (10) extending outwardly from the sleeve on inflation to form a seal with the incision.

6. A surgical device as claimed in claim 1, in which the second seal (12) is provided by an inflatable bladder (12) extending inwardly from the tube or sleeve (4) on inflation to prevent excessive loss of gas through the access port.

7. A surgical device as claimed in claim 6, in which the second seal (12) is operatively connected and mounted within the first seal (10).

* * * * *